(12) United States Patent
Soo et al.

(10) Patent No.: US 9,796,091 B1
(45) Date of Patent: Oct. 24, 2017

(54) SELECTIVE ROBOT DEPLOYMENT

(71) Applicant: X Development LLC, Mountain View, CA (US)

(72) Inventors: Sheryl Soo, Vancouver (CA); Kyle Moore, Woodside, CA (US)

(73) Assignee: X DEVELOPMENT LLC, Mountain View, CA (US)

(*) Notice: Subject to any disclaimer, the term of this patent is extended or adjusted under 35 U.S.C. 154(b) by 42 days.

(21) Appl. No.: 14/827,784

(22) Filed: Aug. 17, 2015

(51) Int. Cl.
| | |
|---|---|
| B25J 9/16 | (2006.01) |
| G06Q 10/10 | (2012.01) |
| B25J 11/00 | (2006.01) |
| G05D 1/00 | (2006.01) |
| G06F 19/00 | (2011.01) |

(52) U.S. Cl.
CPC ........... B25J 9/1689 (2013.01); B25J 11/009 (2013.01); B25J 11/0085 (2013.01); G05D 1/0027 (2013.01); G06F 19/3462 (2013.01); G06Q 10/1095 (2013.01); *G05D 2201/0206* (2013.01); *G05D 2201/0207* (2013.01)

(58) Field of Classification Search
None
See application file for complete search history.

(56) References Cited

U.S. PATENT DOCUMENTS

| | | | |
|---|---|---|---|
| 8,718,837 B2 | 5/2014 | Wang et al. | |
| 8,902,278 B2 | 12/2014 | Pinter et al. | |
| 2012/0316676 A1* | 12/2012 | Fouillade | B25J 11/0005 700/246 |
| 2014/0222206 A1* | 8/2014 | Mead | B25J 9/1697 700/259 |

FOREIGN PATENT DOCUMENTS

| | | |
|---|---|---|
| WO | 2011146254 | 11/2011 |
| WO | 2013176762 | 11/2013 |

OTHER PUBLICATIONS

Tsui, K. M., Desai, M., Yanco, H. A., & Uhlik, C. (Mar. 2011). Exploring Use Cases for Telepresence Robots. In Proceedings of the 6th International Conference on Human-Robot Interaction (HRI). pp. 11-18. ACM.
Kristoffersson, A., Coradeschi, S., & Loutfi, A. (2013). A Review of Mobile Robotic Telepresence. Advances in Human-Computer Interaction. vol. 2013, Article ID 902316, 17 pages.

* cited by examiner

*Primary Examiner* — Rami Khatib
*Assistant Examiner* — Nicholas K Wiltey
(74) *Attorney, Agent, or Firm* — Middleton Reutlinger

(57) ABSTRACT

Methods, apparatus, systems, and computer-readable media are provided for selective robot deployment. In various implementations, a context of a user may be determined based at least in part on a record of one or more computing interactions associated with the user. In various implementations, a robot-performable task of the user may be identified based at least in part on the context. In various implementations, a measure of potential or actual interest of the user in deploying a robot to perform the robot-performable task may be determined. In various embodiments, the robot may be selectively deployed based on the measure of potential or actual interest.

14 Claims, 6 Drawing Sheets

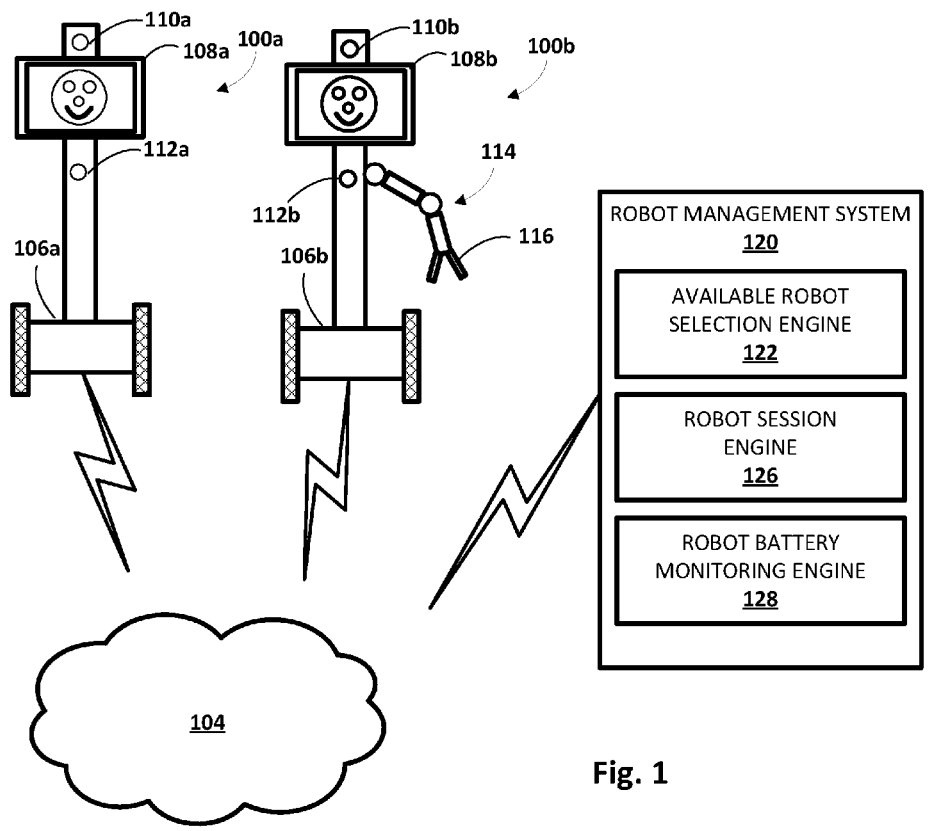
Fig. 1
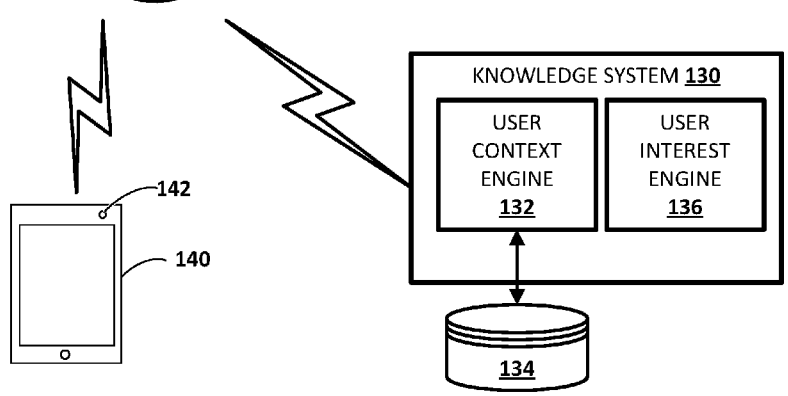

SELECTIVE ROBOT DEPLOYMENT

BACKGROUND

A robot may be used to perform a variety of tasks on behalf of a user. For example, a telepresence robot may be deployed by a user to attend an event such as a meeting on the user's behalf. As another example, medical robot may be deployed, e.g., by medical personnel and/or a patient, to perform tasks/treatments for/on the patient. Oftentimes a user may be unable to perform a task, but may not be well-positioned to deploy and/or control a robot to perform the task on the user's behalf. For example, the user may have forgotten about the task, be incapacitated, or may be busy doing other things (e.g., driving, working, socializing, etc.). Even in situations where a user is able to perform a task, it may be desirable for a robot to perform the task instead, e.g., so that the user can avoid the hassle and/or have something prepared (e.g., toast made, coffee brewed, newspaper fetched, etc.) ahead of when the user needs it.

SUMMARY

The present disclosure is generally directed to methods, apparatus, and computer-readable media (transitory and non-transitory) for automatically selectively deploying robots to perform tasks on behalf of a user based on the user's context. For example, suppose it is determined from a user's electronic calendar or from one or more content items associated with a user that the user is scheduled to attend a meeting, but the user's smart phone indicates that the user is stuck in traffic and will be late. In various implementations, a robot such as a telepresence robot may be deployed (e.g., automatically or in response to user confirmation) from a staging location (e.g., a charging station) to attend the meeting in the user's stead, at least until the user arrives. Once the user arrives at the meeting, in various implementations, the telepresence robot may automatically retreat to the staging location.

In some implementations, a computer implemented method may be provided that includes the steps of: determining, by one or more processors, based at least in part on a record of one or more computing interactions associated with a user, a context of the user; identifying, by the one or more processors, based at least in part on the context, a robot-performable task of potential interest to the user; determining, by the one or more processors, a measure of potential or actual interest of the user in deploying a robot to perform the robot-performable task; and selectively deploying, by the one or more processors, based on the measure of potential or actual interest, a robot to perform the robot-performable task.

This method and other implementations of technology disclosed herein may each optionally include one or more of the following features.

In various implementations, determining the context of the user may include determining that the user is scheduled to perform the robot-performable task. In various implementations, the record of one or more interactions between a user and one or more computing devices may include an electronic calendar associated with the user. In various implementations, the robot may be a telepresence robot, and the robot-performable task may include attending a meeting scheduled on the electronic calendar associated with the user.

In various implementations, the record of one or more interactions between a user and one or more computing devices may include one or more content items created, received, or otherwise consumed by the user. In various implementations, the method may further include determining, by the one or more processors, based on the user's context, that the user will be unable to perform the robot-performable task. In various implementations, the user's context may include a position coordinate provided by a mobile computing device operated by the user.

In various implementations, determining the measure of potential or actual interest may include prompting the user to provide input indicative of actual interest of the user in deploying the robot to perform the robot-performable task. In various implementations, selectively deploying the robot may include deploying the robot to perform the robot-performable task in response to receipt of user input indicative of actual interest of the user in deploying the robot to perform the robot-performable task. In various implementations, the prompting may be performed in response to a determination that a calculated measure of potential interest of the user in deploying the robot to perform the robot-performable task satisfies a threshold.

In various implementations, determining the measure of potential or actual interest may include calculating, based on the user's context, a measure of potential interest of the user in deploying the robot to perform the robot-performable task. In various implementations, selectively deploying the robot may include deploying the robot to perform the robot-performable task in response to a determination that the measure of potential interest satisfies a threshold.

Other implementations may include a non-transitory computer readable storage medium storing instructions executable by a processor to perform a method such as one or more of the methods described above. Yet another implementation may include a robot management system including memory and one or more processors operable to execute instructions, stored in the memory, to implement one or more modules or engines that, alone or collectively, perform a method such as one or more of the methods described above.

It should be appreciated that all combinations of the foregoing concepts and additional concepts described in greater detail herein are contemplated as being part of the subject matter disclosed herein. For example, all combinations of claimed subject matter appearing at the end of this disclosure are contemplated as being part of the subject matter disclosed herein.

BRIEF DESCRIPTION OF THE DRAWINGS

FIG. 1 schematically depicts an example environment in which disclosed techniques may be employed, in accordance with various implementations.

DETAILED DESCRIPTION

Figure 2A:
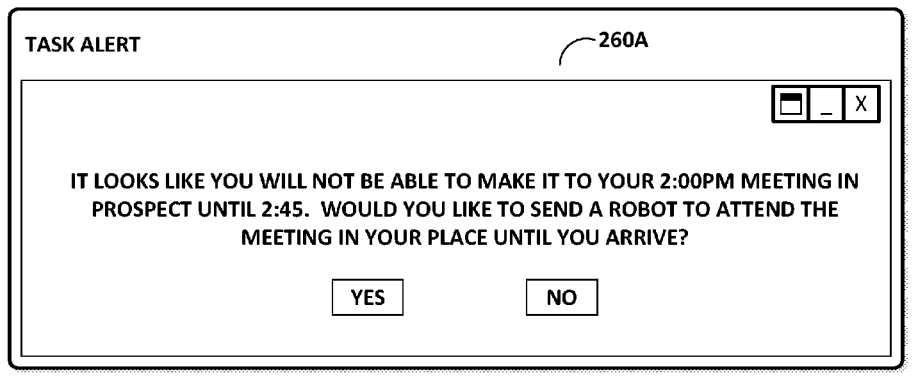
FIGS. 2A, 2B, 3 and 4 depict example graphical user interfaces that may be presented to users to determine their actual interest in having robot-performable tasks performed by one or more robots, in accordance with various implementations.

FIG. 1 is a schematic diagram of an example environment in which selected aspects of the present disclosure may be practiced in accordance with various implementations. One or more robots, such as first robot 100a and second robot 100b, may be in communication via one or more networks 104 with a robot management system 120, a knowledge system 130, and/or a remote computing device 140 operated by a user (not depicted). In various implementations, it may be determined, e.g., by various components of knowledge system 130 and/or robot management system 120, based on a variety of signals (e.g., provided by computing device 140 carried by the user), that the user of computing device 140 is unable or unwilling to perform a task, or that the user is unaware of and/or has forgotten about a task, that may alternatively be performed at least in part by a robot. Such a task may be referred to herein as a "robot-performable" task. In such a situation, robot management system 120 may arrange for one or more of robots (e.g., 100a and 100b) to perform all or as much of the robot-performable task as possible on the user's behalf. In some implementations, robot management system 120 may cause computing device 140 to prompt the user as to whether the user would like the robot-performable task performed by a robot 100, and/or to provide the user with various levels of control over the robot while the robot performs the robot-performable task.

Each robot 100 may take various forms, including but not limited to the telepresence robots depicted in FIG. 1, a robot arm, a humanoid, an animal, an insect, an aquatic creature, a wheeled device, a submersible vehicle, an unmanned aerial vehicle ("UAV"), and so forth. In this example, robots 100a and 100b include motorized wheel assemblies 106a and 106b, respectively, as well as respective display screens 108a and 108b, cameras 110a and 110b, other sensors 112a and 112b, and in at least the case of second robot 100b, a robot arm 114 with an attached end effector 116.

Other sensors 112a and 112b may take various forms, including but not limited to microphones (especially in the case of the telepresence robots 100 depicted in FIG. 1), light sensors (e.g., passive infrared), cameras (including types that sense color and/or depth/position), force sensors, pressure sensors, proximity sensors (also referred to as "distance sensors"), torque sensors, bar code readers, radio frequency identification ("RFID") readers, radars, range finders, accelerometers, gyroscopes, compasses, position coordinate sensors (e.g., global positioning system ("GPS"), Wi-Fi triangulation, etc.), speedometers, edge detectors, and so forth. While sensors 112a-b are depicted as being integral with robots 100a-b, this is not meant to be limiting. In some implementations, sensors 112 may be located external to, but may be in direct or indirect communication with, robots 100a-b, e.g., as standalone units or as part of separate robot management system 120.

As used herein, "end effector" 116 may refer to a variety of tools that may be operated by robot 100 in order to accomplish various tasks. For example, some robots may be equipped with an end effector 116 that takes the form of a claw with two opposing "fingers" or "digits." Such as claw is one type of "gripper" known as an "impactive" gripper. Other types of grippers may include but are not limited to "ingressive" (e.g., physically penetrating an object using pins, needles, etc.), "astrictive" (e.g., using suction or vacuum to pick up an object), or "contigutive" (e.g., using surface tension, freezing or adhesive to pick up object). More generally, other types of end effectors may include but are not limited to drills, brushes, force-torque sensors, cutting tools, deburring tools, welding torches, and so forth. In some implementations, end effector 116 may be removable, and various types of modular end effectors may be installed onto arm 114 of second robot 100b, depending on the circumstances.

Robots 100a and 100b may be controlled and/or managed to various degrees by robot management system 120. Robot management system 120 may include one or computing systems connected by one or more networks (not depicted) that control and/or manage operation of robots 100 to various degrees. An example of such a computing system is depicted schematically in FIG. 6. Various modules or engines may be implemented as part of robot management system 120 as software, hardware, or any combination of the two. For example, in FIG. 1, robot management system 120 includes an available robot selection engine 122, a robot session engine 126, and a robot battery monitoring engine 128.

While robots 100a-b and robot management system 120 are depicted separately in FIG. 1, this is not meant to be limiting. In various implementations, one or more aspects (e.g., modules, engines, etc.) depicted in FIG. 1 as implemented on one of robot 100 or robot management system 120 may be implemented on the other, may be distributed across both, and/or may be distributed across one or both in combination with other components not depicted in FIG. 1. In implementations where robot 100 and robot management system 120 are separate, they may communicate over one or more wired or wireless networks 104 or using other wireless technology, such as radio, Bluetooth, infrared, etc.

Available robot selection engine 122 may be configured to determine whether one or more of robots 100a-b is available perform various robot tasks that may be identified by knowledge system 130 (as will be described below), and, if so, to select robot 100a or 100b to perform the task. As used herein, a robot is "available" for a given time period if it is not performing and/or scheduled to perform a task during the given time period. For example, if a robot task is to remotely attend a meeting for the next thirty minutes, a robot would be available for that task if it is not currently performing a task and is not scheduled to perform a task for the next thirty minutes. In some implementations, available robot selection engine 122 may determine if a robot is available to perform the task based on comparing an explicit or estimated time period for the task to a current status and/or schedule of the robot. In some of those implementations, the schedule of the robot may be maintained in one or more databases remote from the robot such as a relational database. Additionally or alternatively, in some implementations, the schedule of a robot may be maintained at the robot itself and the available robot selection engine 122 may communicate with the robot to determine if it is available to perform an identified robot task.

In some implementations, available robot selection engine 122 may determine that a robot is suited to perform a task if the robot is available during a time period of the task. In some other implementations, available robot selection engine 122 may determine a robot is suited to perform the task based on comparing at least one additional property of the robot task to a property of the robot. For example, a robot task to "remotely attend a meeting" may be mapped to a required robot property of "telepresence robot" or required robot attributes of "display", "camera", and "microphone." By contrast, a robot task of "deliver object" may be mapped to a required robot property of "includes gripper", required robot property of "includes container", and/or to one or more particular robots (e.g., telepresence robot 100b). Also, for example, a robot task where the user has explicitly indicated a need for a gripper may be mapped to a required robot property of "includes gripper." Mappings between tasks and/or properties of tasks and associated robot properties and/or robots may be provided in memory of available robot selection engine 122 and/or in one or more databases accessible by available robot selection engine 122. As yet another example of determining a robot is suited to perform a task, an expected duration and/or expected battery load of a robot task may be compared to a charge level of a battery of a candidate robot (e.g., as may be provided by robot battery monitoring engine 128) to determine if the candidate robot is likely to have at least a threshold charge level of battery at the completion of the task. If the candidate robot is likely to have at least the threshold charge level at the completion of the task, available robot selection engine 122 may determine it is suited to perform the task.

In some implementations where the user operates computing device 140 to maintain at least some control over robot 100 to perform a robot-performable task, robot session engine 126 may initiate the establishment of a session between the selected robot and computing device 140 operated by the user assigned the task. For example, robot session engine 126 may provide a unique identifier of the selected robot to computing device 140 and/or provide a unique identifier of computing device 140 to the selected robot to enable the selected robot and computing device 140 to establish a session with one another. The unique identifiers may include, for example, one or more of an internet protocol (IP) address, media access control (MAC) address, and/or other standardized or non-standardized addresses. In many implementations, robot session engine 126 and/or another component may serve as an intermediary in establishing the session, especially in situations in which users and/or robots are behind a firewall, e.g., so that robot session engine 126 may ensure robot resources are being allocated properly. In other implementations the selected robot and the computing device may establish a session with one another without an intermediary. In some embodiments, robot session engine 126 may manage security between a selected robot and computing device, such as handling authentication, preventing unauthorized users from operating the robot, monitoring for unauthorized robots (e.g., robots masquerading as legitimate robots), etc.

An established session between computing device 140 and a robot (e.g., 100a or 100b) may be an interactive data exchange between the computing device and the robot via one or more networks 104. The data exchanged during the session may include, for example, data transmitted from the robot to computing device 140 such as sensor data from the robot (e.g., a video and/or audio feed from a camera and microphone of the robot), location data from a location sensor of the robot that provides an indication of the location of the robot, etc. The data exchanged during the session may additionally and/or alternatively include, for example, data transmitted from computing device 140 to the robot such as a video and audio feed provided by a camera 142 and microphone (not depicted) of computing device 140, control commands to direct the robot to a particular location and/or a particular orientation in response to input provided at computing device 140, etc.

In implementations where a selected robot is capable of autonomous navigation, available robot selection engine 122 may dispatch the robot to a location based on an initiation time of the robot task. For example, for a task that is to start immediately, the available robot selection engine 122 may dispatch the robot to a location for the robot task as soon as possible. For a task that scheduled to be performed at a particular time in the future, available robot selection engine 122 may dispatch the robot so that it arrives at a location for the robot task at or in advance of the scheduled time. In some implementations, available robot selection engine 122 may dispatch the robot to the location for the robot task in advance of robot session engine 126 initiating establishment of the session between the robot and computing device 140 of the user.

Robot battery monitoring engine 128 may be configured to monitor a charge level of one or more batteries of one or more robots 100. In some implementations, robot battery monitoring engine 128 may communicate data indicative of the charge level to available robot selection engine 122. In some implementations, available robot selection engine 122 may select an available robot for an identified task based at least in part on determining a charge level of a battery of the available robot is sufficient to last an anticipated duration of the identified task. If a robot currently performing a task is running low on charge, robot session engine 126 may initiate termination of a session between the task-engaged robot and computing device 140 and direct the robot to a charging station to enable charging of the battery of the robot.

In some implementations, robot battery monitoring engine 128 may determine the need for a robot to charge based on a charge level of a battery of the telepresence robot failing to satisfy a threshold charge level, such as a threshold percentage, amp hours, or other indication of charge level. In some implementations, robot battery monitoring engine 128 may determine the need for a robot to perform the charging task based on identifying an anticipated end time of the robot task of the user and determining a charge level of the battery at the anticipated end time will fail to satisfy a threshold charge level. For example, the charge level of the battery at the anticipated end time may be estimated based on a current charge level of the battery and anticipated battery drain that will occur by the anticipated end time.

The anticipated battery drain that will occur by the anticipated end time may be determined with reference to a formula and/or a table and may take into account an amount of time, properties of the current task, etc. Properties of the current task may include, for example, the current or anticipated state of components of robot 100 such as whether display screen 108 of robot 100 is active and/or will remain active, whether and/or to what extent operation components of robot 100 are currently being operated to drive motorized wheel assemblies 106 or other components of robot 100, whether and/or to what extent motors of robot 100 will be driven to drive components of the robot 100, etc. In some implementations, robot battery monitoring engine 128 and/or available robot selection engine 122 may examine future reservations for a particular robot to determine that the robot will have sufficient charge to fulfill those future reservations. Suppose a robot is booked for an hour at 4 pm, and that the robot only has one hour of battery at 3 pm. Robot battery monitoring engine 128 and/or available robot selection engine 122 may not allow another user to operate the robot for forty five minutes at 3 pm because the robot would not be able to charge sufficiently in the remaining fifteen minutes.

Robot battery monitoring engine 128 and/or available robot selection engine 122 may utilize one or more sources to identify an anticipated end time for a robot task. For example, knowledge system 130 may have access to electronically-stored calendar data that is personal to the user. Such data may be used to identify a scheduled end time of the robot task of the user. Additionally or alternatively, a user may provide explicit input to robot management system 120 that indicates an anticipated duration or an end time. Also, for example, mappings between tasks and/or properties of tasks and anticipated durations for the tasks may be provided in memory of available robot selection engine 122 and/or in one or more databases accessible by available robot selection engine 122.

In some implementations, the anticipated durations of the tasks may have been determined based on observed durations of past tasks. For example, an anticipated task duration could be determined based on the average length of "similar" tasks performed for either this user or an aggregate of other users in the past. Whether two tasks are considered "similar" may be determined in various ways, such as manually (e.g., a user manually provides an indication that two or more tasks are similar) or based on machine learning techniques.

Robot-performable tasks may be identified by knowledge system 130, e.g., based on various signals pertaining to a context of the user that operates computing device 140. Knowledge system 130 may include one or computing systems connected by one or more networks (not depicted) that may have aspects to various sources of data pertaining to the user's context. An example of such a computing system is depicted schematically in FIG. 6. Various modules or engines may be implemented as part of robot management system 120 as software, hardware, or any combination of the two. For example, in FIG. 1, knowledge system 130 includes a user context engine 132 and a user interest engine 136.

User context engine 132 may be configured to create, maintain, and/or access one or more records of interactions between users and computing devices. In some implementations, the records may be stored in one or more databases, such as index 134. A user may have a variety of different interactions with computing devices that effectively define at least part of the user's context. For example, a corpus of content created, received, or otherwise consumed by a user may be analyzed to identify aspects of the user's schedule, entities with which the user is familiar, and so forth. The user additionally or alternatively may maintain one or more electronic calendars which may provide additional contextual data about a user (e.g., the user is scheduled to be at location X at time Y with one or more other persons). Additionally or alternatively, the user may maintain (e.g., in association with the user's calendar or separately) reminders, tasks, notes, contacts, and so forth. Additionally or alternatively, the user's activity on one or more social networks may be accessible by user context engine 132.

User context engine 132 may also obtain information about a user's context from computing device 140 that is carried and/or operated by the user. For example, computing device 140 may come in various portable forms, such as a smart phone, smart watch, fitness tracker, smart glasses, vehicle navigation system, and so forth. Such devices may include a variety of sensors, including but not limited to coordinate sensors (e.g., global positioning system or "GPS," various types of triangulation, such as Wi-Fi triangulation, etc.), accelerometers, gyroscopes, thermometers, heart rate monitors, glucose sensors, barometers, magnetometers, proximity sensors, light sensors, humidity sensors, pedometers, fingerprint sensors, and so forth. Any one of these sensors may provide a signal that, alone or in combination with other sensor signals, may be used to ascertain aspects of a user's context. For example, GPS signals from a user's phone may, over time in the aggregate, reveal that the user typically arrives at work within a particular window of time. On a particular day near the end of that window of time, a GPS signal from the user's phone may reveal that the user is currently far away from work. An accelerometer signal from the user's smart phone may reveal that the user is repeatedly stopping and moving, which may suggest the user is stuck in traffic. Based on these signals, it may be determined that the user likely will be late to work. Consequently, a robot-performable task of "report to user's cubicle for morning announcements" may be identified and assigned to a telepresence robot at the user's office.

User interest engine 136 may be configured to calculate (e.g., predict) and/or determine, e.g., based on user context data obtained from user context engine 132, a measure of potential and/or actual interest by the user in deploying a robot to perform a robot-performable task, e.g., on behalf of the user. A measure of "potential" interest by the user in having a robot-performable task performed by a robot may be a best "guess," based on various data points, of whether the user would want to have the robot perform the task. A measure of "actual" interest by the user in having a robot-performable task performed by a robot may be a more definitive measure determined from explicit input provided by the user.

In some implementations, user interest engine 136 may calculate (e.g., predict) a user's potential interest in having a robot-performable task performed based on the user's context. Suppose a user's calendar reveals that the user is scheduled to be in a particular location at a particular time. Suppose further that one or more content items consumed by the user reveal that the user is to meet with someone named Dave, and the user's employment profile (e.g., accessible by user context engine 132) reveals that Dave is the user's boss. The user's interest in attending such a meeting would presumably be quite high. Now, suppose the just before the meeting, user context engine 132 learns, e.g., from a signal provided by computing device 140, that the user is stuck in traffic and will not be able to make the meeting on time. User interest engine 136 may calculate, e.g., based on a combination of these data points, a measure of potential interest by the user in attending the meeting as being very high. In some implementations, user interest engine 136 may provide or otherwise make this measure available to various components of robot management system 120, such as available robot selection engine 122.

In various implementations, a user's actual interest in having a robot-performable task performed on behalf of the user may be determined, e.g., by user interest engine 136, by communicating directly or indirectly with computing device 140 to cause computing device 140 to provide the user with a prompt, such as "DEPLOY ROBOT TO PERFORM TASK XXX?" In some implementations, such as when the user is driving or otherwise travelling, the user may be provided with an audible prompt. The user may be able to respond in kind, e.g., through voice recognition implemented on computing device 140.

Prompting a user to determine whether they have actual interest in a robot performing a task may be disruptive. Selectively prompting the user only when the potential interest is sufficiently high may avoid inundating the user with too many communications. Accordingly, in some implementations, a prompt to ascertain a user's actual interest in having a robot perform a task may only be presented to the user if user interest engine 136 determines that a measure of potential user interest in having the robot-performable task performed by the robot satisfies a first threshold. But, in some implementations, if the measure of potential user interest in having the robot-performable task performed by the robot satisfies a second, presumably much higher threshold, user interest engine 136 may request that available robot selection engine 122 automatically deploy a robot to perform the task, without prompting the user first.

Such thresholds may be determined in various ways. In some implementations, the thresholds may be learned (e.g., using a machine learning classifier) over time, e.g., by keeping track of how often users accept offers to have robots perform tasks. Thresholds may vary depending on the nature of the tasks, as well, and some types of tasks (e.g., making coffee) may have lower thresholds than others (e.g., wash car). In some implementations, if a user accepts an offer to have a robot perform a particular task or type of task often enough, the user may be prompted as to whether they'd like that task or type of task to be performed automatically in the future. Those users may continue to be notified that the task is being performed e.g., so that they can disable auto-performance in the future if desired.

FIG. 2A depicts an example graphical user interface 260A that may be presented to a user, e.g., on computing device 140, at the request of knowledge system 130 and/or robot management system 120, to determine whether the user has actual interest in deploying a robot to perform a task on the user's behalf. In this example, it has been determined, e.g., by user context engine 132 based on a user's calendar, that the user has a meeting scheduled in "Prospect" at 2:00 pm. It has been further determined, e.g., by user context engine 132 based on the user's current location (e.g., as provided by a coordinate determination mechanism of computing device 140), that the user will be at least forty-five minutes late. It also has been determined, e.g., by user interest engine 136, that the user has at least some measure of potential interest in attending the meeting, e.g., based on the fact that the user deliberately created a calendar entry (e.g., as opposed to a user's calendar being auto-populated). The measure of potential interest of the user was sufficient to cause user interest engine 136 or another component, such as available robot selection engine 122 of robot management system 120, to cause computing device 140 to render the graphical user interface depicted in FIG. 2A.

In FIG. 2A, the user is asked to answer YES or NO to the question, "WOULD YOU LIKE TO SEND A ROBOT TO ATTEND THE MEETING IN YOUR PLACE UNTIL YOU ARRIVE?" In response to the user clicking or otherwise selecting YES, available robot selection engine 122 may take various actions. In some implementations, available robot selection engine 122 may simply select whichever of first robot 100a or second robot 100b has sufficient battery charge (e.g., as determined by robot battery monitoring engine 128) to travel to and attend the meeting for at least forty-five minutes.

Figure 2B:
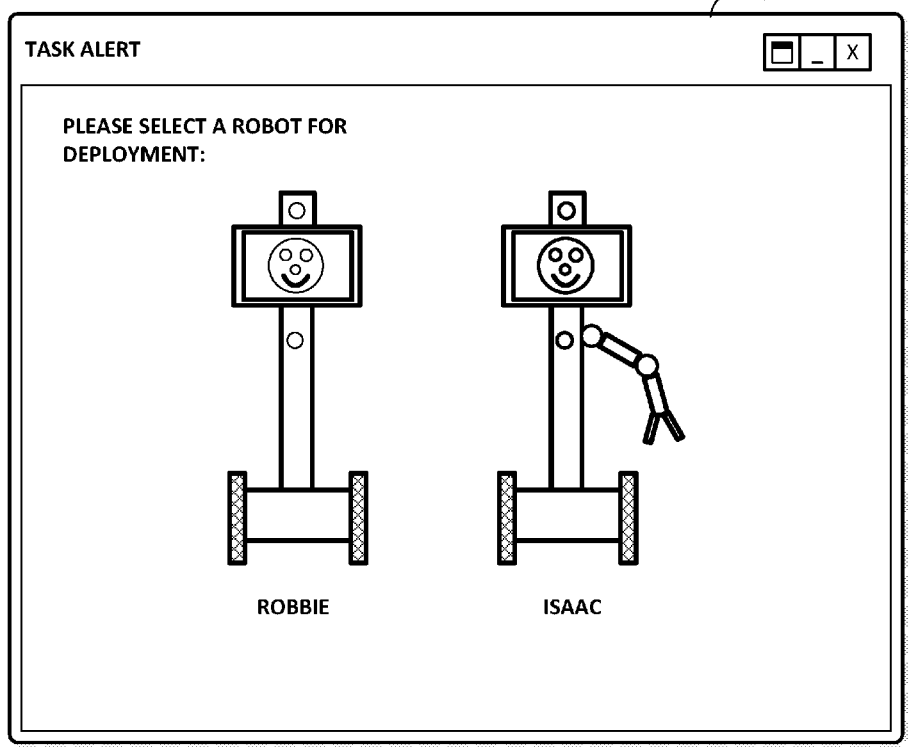

In some implementations, available robot selection engine 122 may automatically select the best-suited robot for the task. For example, both first robot 100a and second robot 100b may have components that make the robots suitable to act as telepresence robots at a meeting. However, second robot 100b may include extra components—namely, its robot arm 114 and end effector 116—that enable it to perform more complex tasks. Rather than sending second robot 100b to the meeting where components such as its robot arm 114 or end effector 116 are not needed, available robot selection engine 122 may send first robot 100a to the meeting instead. That way, second robot 100b and its more advance capabilities remain available for use by others with more demanding needs. In other implementations, available robot selection engine 122 may provide the user with a prompt such as the graphical user interface 260B depicted in FIG. 2B, which prompts the user to select whether the user would prefer to deploy a robot named "ROBBIE" or a robot named "ISAAC."

Figure 3:
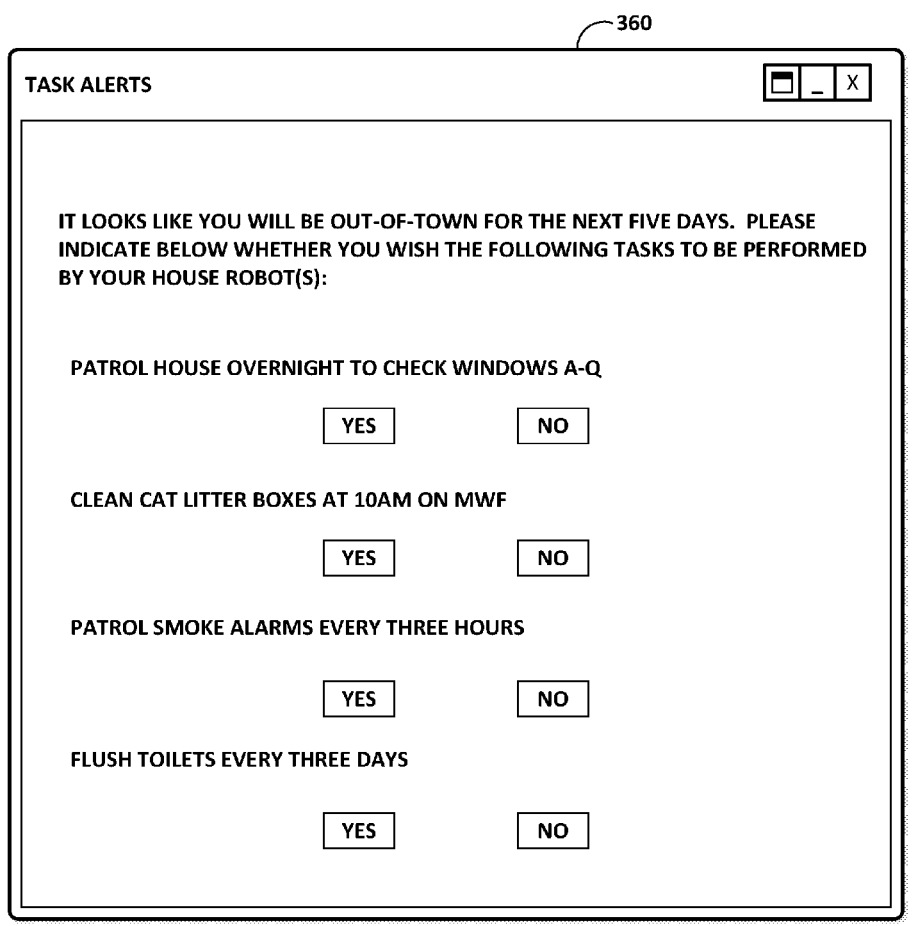

FIG. 3 depicts another example of a graphical user interface 360 that may be presented to a user to determine whether the user has actual interest in having a robot perform a variety of tasks at the user's home while the user is out of town. In this example, graphical user interface 360 may be presented to the user on a determination, e.g., by computing device 140 and/or available robot selection engine 122 based on the user's context, that the user is travelling away from home. Such a determination may be made based on one or more signals pertaining to the user's context, such one or more calendar entries made by the user, other user content items created by and/or consumed by the user, a signal from a GPS sensor on the user's smart phone that the user is outside of the user's resident city, one or more signals from an automated home thermostat (e.g., allowing the user's home to reach temperatures that would be uncomfortable to an occupant), and so forth.

In graphical user interface 360, the user is presented with a variety of robot-performable tasks that may be performed by one or more robots at the user's home. A first robot-performable task would be for a robot to patrol the user's house to check windows overnight. A second robot-performable task would be for a robot to clean one or more cat litter boxes at a particular time on particular days of the week. A third robot-performable task would be for a robot to patrol smoke alarms in the user's house every few hours. A fourth robot-performable task would be for a robot to flush toilets at the user's house every so often. The user may operate graphical user interface 360 to select YES for the robot-performable tasks that the user wishes be performed by one or more robots, and NO for the robot-performable tasks the user elects not to have performed while the user is out of town. The robot-performable tasks that are made available in an interface such as 360 may be selected based what robots a user possesses and capabilities of those robots, tasks the user explicitly creates, and so forth.

Figure 4:
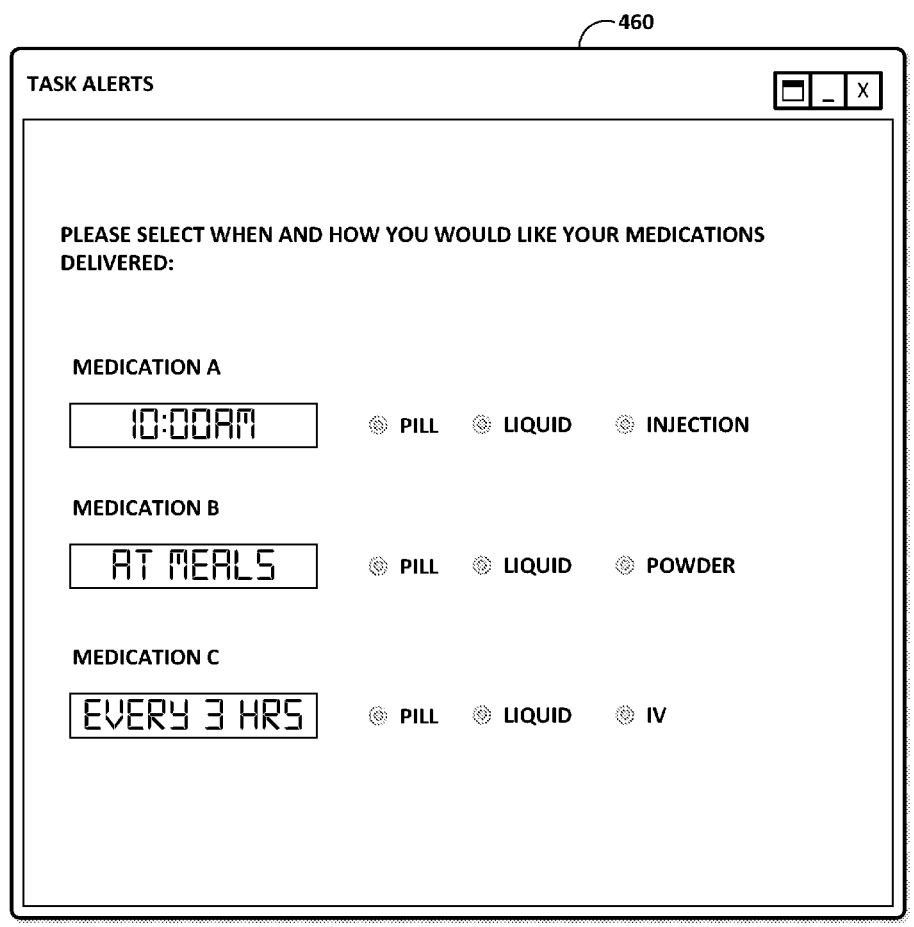

FIG. 4 depicts another example of a graphical user interface 460 that may be presented to a user to determine whether the user has actual interest in having a robot deliver various medications to the user (or someone under the user's care). In this example, graphical user interface 460 may be presented to the user on a determination, e.g., by computing device 140 and/or available robot selection engine 122 based on the user's context, that the user will be unable to obtain the medications himself or herself. For example, a user's context may reveal that the user is under strict bedrest. The medications presented, as well as the accompanying delivery options for each medication, may also be determined from a user's context, e.g., from a prescription identified by or provided to user context engine 132.

In graphical user interface 460, the user is presented with a variety of robot-performable tasks pertaining to medicine delivery. A first robot-performable task would be for a robot to deliver MEDICATION A to a user. In the interface, this task is set to be performed at ten o'clock in the morning, but that may be editable to whatever time the user desires. A user may select whether the medicine is delivered in pill or liquid form (e.g., which a bedridden user may still be capable of taking), or whether MEDICATION A should be injected by a robot. A second robot-performable task would be for a robot to deliver MEDICATION B to the user. The second robot-performable task includes slightly different delivery options ("POWDER" instead of "INJECTION"). A third robot-performable task would be for a robot to deliver MEDICATION C to the user, and includes an option for intravenous, or "IV," delivery.

Figure 5:
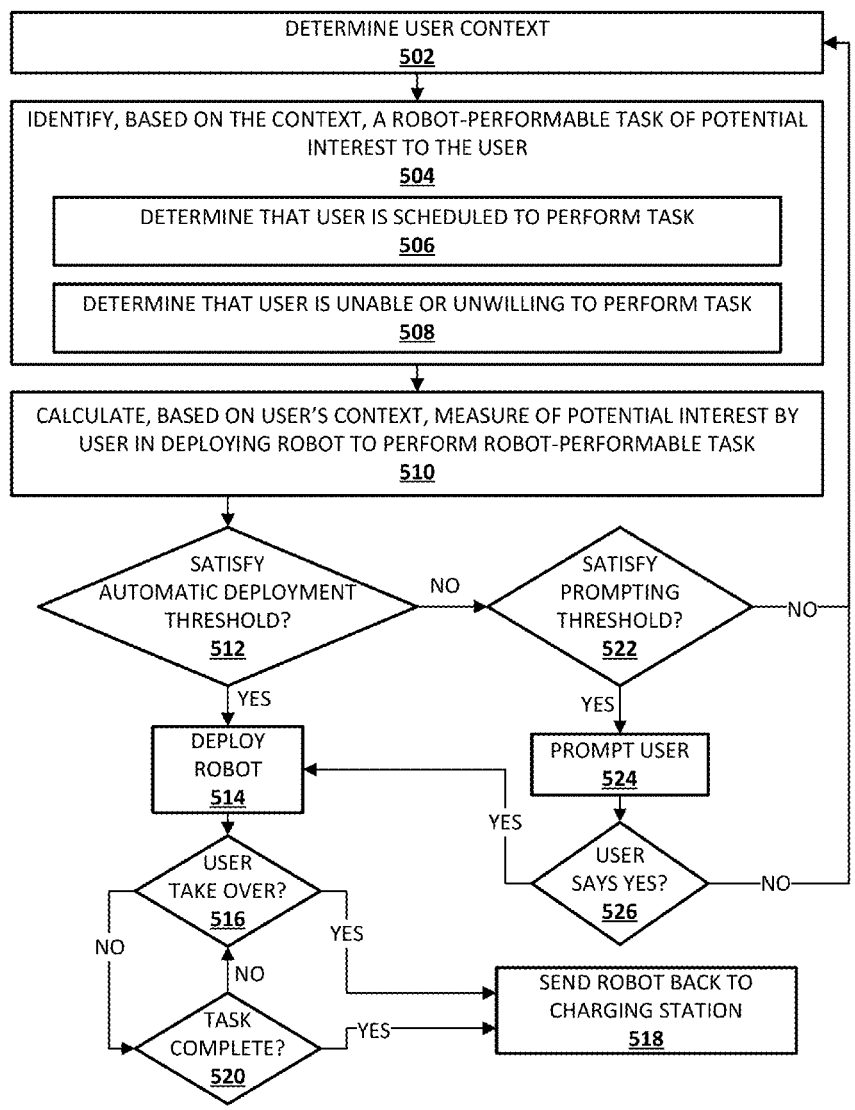
FIG. 5 depicts an example method for selectively deploying a robot to perform a task, in accordance with various implementations.

Referring now to FIG. 5, an example method 500 of selectively deploying a robot to perform a robot-performable task is described. For convenience, the operations of flow charts are described with reference to a system that performs the operations. This system may include various components of various computer systems, including computing elements of robot 100, robot management system 120, knowledge system 130, and/or computing device 140. Moreover, while operations of method 500 are shown in a particular order, this is not meant to be limiting. One or more operations may be reordered, omitted or added.

At block 502, the system may determine a user's context, e.g., based on data provided by user context engine 132. At block 504, the system may identify, based on the user context determined at block 502, a robot-performable task of potential interest of the user. For example, the system may use the user's context to identify, at block 506, a task the user is supposed to perform. For example, the system may determine from the user's calendar that the user is scheduled to attend an event at a particular time and location. At block 508, the system may determine that the user will be unable to perform, or likely may be unwilling to perform, the task identified at block 506. For example, the system may determine, e.g., based on the user's GPS signal, that the user is too far away to attend the event in any reasonable amount of time. In such instance, the task of attending the event may be identified as a robot-performable task of potential interest to the user.

At block 510, the system may calculate, based on the user context determined at block 502, a measure of potential interest by the user in deploying a robot to perform the robot-performable task identified at block 504. At block 512, the system may determine whether the measure calculated at block 510 satisfies one or more automatic robot deployment thresholds. If the answer at block 512 is yes, then method 500 may proceed to block 514.

At block 514, the system may deploy one or more robots to perform the task identified at block 504. For example, a telepresence robot may be deployed to attend a meeting in the user's place, at least until the user arrives at the meeting. At block 516, the system may determine whether the user is available to take over performance of the task from the one or more robots. For example, the user may arrive late at the meeting, at which point the telepresence robot's presence is no longer necessary. The determination at block 516 may be made based on a variety of signals pertaining to the user's context. For example, the user's computing device (e.g., 140, which may be a mobile computing device) may provide a position coordinate signal that the system uses to determine that the user is proximal to the one or more robots and thus is able to take over performance of the task. Or, the user's computing device may transmit a wireless signal (e.g., Bluetooth, Wi-Fi direct, RFID, etc.) directly to the one or more robots, or to robot management system 120, that indicates the user is proximal the one or more robots and able to take over performance of the task.

If the answer at block 516 is yes, then method 500 may proceed to block 518, at which point the system sends the one or more robots back to their respective staging areas (e.g., charging stations). However, if the answer at block 516 is no, then method 500 may proceed to block 520. At block 520, the system may determine whether the robot(s) have completed performing the robot-performable task. If the answer is no, then method 500 may proceed back to block 516. However, if the answer at block 520 is yes, then method 500 may proceed to block 518, and the one or more robots may be sent back to their respective charging stations.

Back at block 512, if the measure of potential user interest in having one or more robots perform the robot-performable task identified at block 504 does not satisfy any automatic deployment thresholds, then method 500 may proceed to block 522. At block 522, the system m may determine whether the measure of potential user interest satisfies one or so-called "user prompting" thresholds (which may be lower than the automatic deployment threshold of block 512). If the answer is no, the identified robot-performable task is not likely something the user is interested in, and method 500 may proceed back to block 502. However, if the answer at block 522 is yes, then method 500 may proceed to block 524.

At block 524, the system may prompt the user, or may cause a prompt to be presented to the user (e.g., visually as shown in FIGS. 2A, 2B, 3, and 4, audibly, in a haptic manner, etc.) to determine the user's actual interest in having the robot-performable task that was identified at block 504 performed by one or more robots. At block 526, the system may determine whether the user confirmed actual interest in having one or more robots perform the robot-performable task identified at block 504. If the answer is no, then method 500 may proceed back to block 502. If the answer at block 526 is yes, however, then method 500 may proceed to block 514, and one or more robots may be deployed to perform the robot-performable task.

Figure 6:
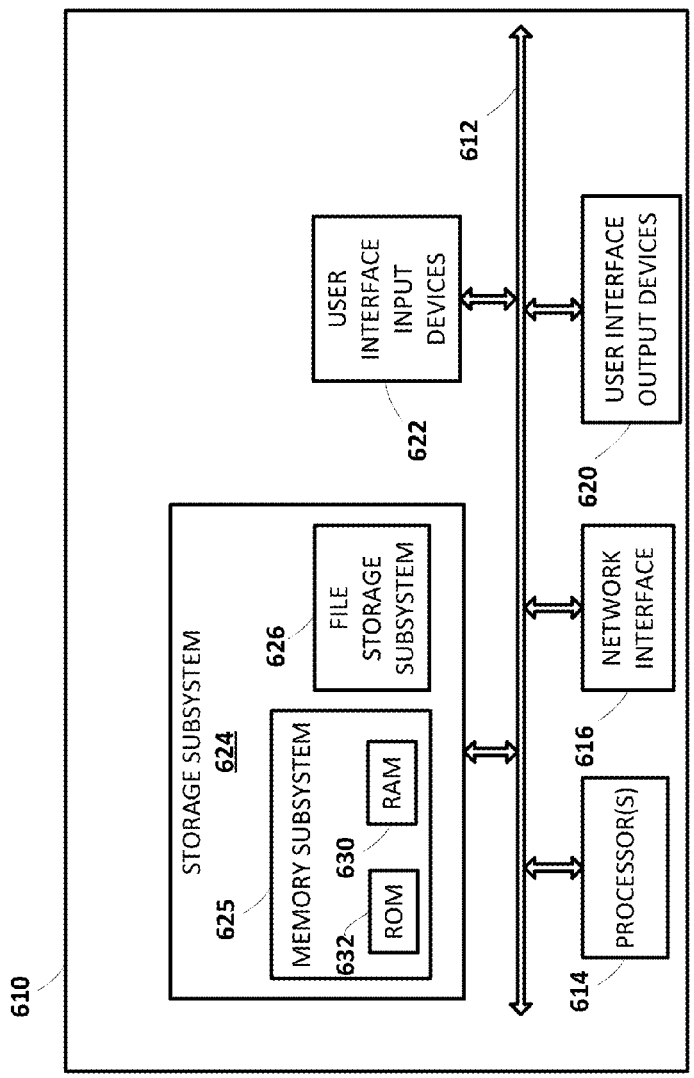
FIG. 6 schematically depicts an example architecture of a computer system.

FIG. 6 is a block diagram of an example computer system 610. Computer system 610 typically includes at least one processor 614 which communicates with a number of peripheral devices via bus subsystem 612. These peripheral devices may include a storage subsystem 624, including, for example, a memory subsystem 625 and a file storage subsystem 626, user interface output devices 620, user interface input devices 622, and a network interface subsystem 616. The input and output devices allow user interaction with computer system 610. Network interface subsystem 616 provides an interface to outside networks and is coupled to corresponding interface devices in other computer systems.

User interface input devices 622 may include a keyboard, pointing devices such as a mouse, trackball, touchpad, or graphics tablet, a scanner, a touchscreen incorporated into the display, audio input devices such as voice recognition systems, microphones, and/or other types of input devices. In general, use of the term "input device" is intended to include all possible types of devices and ways to input information into computer system 610 or onto a communication network.

User interface output devices 620 may include a display subsystem, a printer, a fax machine, or non-visual displays such as audio output devices. The display subsystem may include a cathode ray tube (CRT), a flat-panel device such as a liquid crystal display (LCD), a projection device, or some other mechanism for creating a visible image. The display subsystem may also provide non-visual display such as via audio output devices. In general, use of the term "output device" is intended to include all possible types of devices and ways to output information from computer system 610 to the user or to another machine or computer system.

Storage subsystem 624 stores programming and data constructs that provide the functionality of some or all of the modules described herein. For example, the storage subsystem 624 may include the logic to perform selected aspects of method 500, and/or to implement one or more aspects of available robot selection engine 122, robot session engine 126, robot battery monitoring engine 128, user context engine 132, and/or user interest engine 136. Memory 625 used in the storage subsystem 624 can include a number of memories including a main random access memory (RAM) 630 for storage of instructions and data during program execution and a read only memory (ROM) 632 in which fixed instructions are stored. A file storage subsystem 626 can provide persistent storage for program and data files, and may include a hard disk drive, a CD-ROM drive, an optical drive, or removable media cartridges. Modules implementing the functionality of certain implementations may be stored by file storage subsystem 626 in the storage subsystem 624, or in other machines accessible by the processor(s) 614.

Bus subsystem 612 provides a mechanism for letting the various components and subsystems of computer system 610 communicate with each other as intended. Although bus subsystem 612 is shown schematically as a single bus, alternative implementations of the bus subsystem may use multiple busses.

Computer system 610 can be of varying types including a workstation, server, computing cluster, blade server, server farm, smart phone, smart watch, smart glasses, set top box, tablet computer, laptop, or any other data processing system or computing device. Due to the ever-changing nature of computers and networks, the description of computer system 610 depicted in FIG. 6 is intended only as a specific example for purposes of illustrating some implementations. Many other configurations of computer system 610 are possible having more or fewer components than the computer system depicted in FIG. 6.

In situations in which the systems described herein collect personal information about users, or may make use of personal information, the users may be provided with an opportunity to control whether programs or features collect user information (e.g., information about a user's social network, social actions or activities, profession, a user's preferences, or a user's current geographic location), or to control whether and/or how to receive content from the content server that may be more relevant to the user. Also, certain data may be treated in one or more ways before it is stored or used, so that personal identifiable information is removed. For example, a user's identity may be treated so that no personal identifiable information can be determined for the user, or a user's geographic location may be generalized where geographic location information is obtained (such as to a city, ZIP code, or state level), so that a particular geographic location of a user cannot be determined. Thus, the user may have control over how information is collected about the user and/or used.

While several implementations have been described and illustrated herein, a variety of other means and/or structures for performing the function and/or obtaining the results and/or one or more of the advantages described herein may be utilized, and each of such variations and/or modifications is deemed to be within the scope of the implementations described herein. More generally, all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific implementations described herein. It is, therefore, to be understood that the foregoing implementations are presented by way of example only and that, within the scope of the appended claims and equivalents thereto, implementations may be practiced otherwise than as specifically described and claimed. Implementations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure

What is claimed is:

1. A method, comprising:
   determining, by one or more processors, based at least in part on a record of one or more computing interactions associated with a user, that the user is scheduled to attend an event at a particular time and location;
   determining, by one or more of the processors, based on one or more schedules associated with one or more robots in a database, that attendance to the event is a robot-performable task performable by at least one of the one or robots in lieu of the user;
   determining, by one or more of the processors, based on a position coordinate provided by a mobile computing device operated by the user, that the user will be unable to attend the event; and
   deploying, by one or more of the processors, based on the determination that the user will not be able to attend the event based on the position coordinate a given robot of the one or more robots to attend the event at the particular time and location in lieu of the user.

2. The method of claim 1, wherein the record of one or more computing interactions associated with the user includes an electronic calendar associated with the user.

3. The method of claim 2, wherein the robot comprises a telepresence robot, and the event comprises a meeting scheduled on the electronic calendar associated with the user.

4. The method of claim 1, wherein the record of one or more computing interactions associated with the user includes user content created, received, or consumed by the user.

5. The method of claim 1, further comprising:
   predicting, by one or more of the processors, a measure of potential interest of the user in deploying a robot of the one or more robots to attend the event, wherein the measure of potential interest is predicted implicitly based on the record of one or more computing interactions associated with the user; and
   wherein the deploying is further based on satisfaction, by the predicted measure of potential interest, of one or more potential interest thresholds.

6. The method of claim 1, further comprising:
   providing, by one or more of the processors, output via an output device of the mobile computing device operated by the user, wherein the output prompts the user to provide input indicative of actual interest of the user in deploying the robot to attend the event; and
   wherein the deploying is further based on receipt, at one or more input devices of the mobile computing device operated by the user, of user input indicative of actual interest of the user in deploying the robot to attend the event.

7. A method comprising:
identifying, by one or more processors, a robot-performable task of potential interest to a user;
predicting, by one or more of the processors, a measure of potential interest of the user in deploying a robot to perform the robot-performable task, wherein the measure of potential interest is predicted without explicit user input based on a record of one or more computing interactions associated with the user;
based on a determination that the predicted measure of potential interest satisfies a first interest threshold, selecting, by one or more of the processors, based on one or more schedules associated with one or more robots in a database, a given robot to perform the robot-performable task in lieu of the user; and
deploying, by one or more of the processors, the given robot to perform the robot-performable task in lieu of the user.

8. The method of claim 7, wherein the record of one or more computing interactions includes an electronic calendar associated with the user.

9. The method of claim 8, wherein the given robot comprises a telepresence robot, and the robot-performable task comprises attending a meeting scheduled on the electronic calendar associated with the user.

10. The method of claim 7, wherein the record of one or more computing interactions includes one or more content items created, received, or consumed by the user.

11. The method of claim 7, further comprising:
based on a determination that the predicted measure of potential interest satisfies the first interest threshold and not a second interest threshold that is greater than the first interest threshold, providing, by one or more of the processors, output via an output device of a computing device operated by the user, wherein the output prompts the user to provide explicit input indicative of actual interest of the user in deploying the robot to perform the robot-performable task in lieu of the user;
wherein the robot is deployed to perform the robot-performable task based on receipt, at one or more input devices of the computing device operated by the user, of explicit user input indicative of actual interest of the user in deploying the robot to perform the robot-performable task.

12. A system comprising:
one or more computers configured to perform operations comprising:
determining, based at least in part on one or more signals generated by a computing device operated by a user, that the user is scheduled to attend an event at a particular time and location;
determining, based on one or more schedules associated with one or more robots in a database, that attendance to the event is a robot-performable task performable by at least one of the one or robots in lieu of the user;
determining, based on a position coordinate provided by the computing device operated by the user, that the user will be unable to attend the event; and
deploying, based on the determination that the user will not be able to attend the event based on the position coordinate a given robot of the one or more robots to attend the event at the particular time and location in lieu of the user.

13. The system of claim 12, wherein the one or more computers are further configured to perform operations comprising:
based on the determination that the user will not be able to attend the event, prompt the user to provide input indicative of actual interest of the user in deploying the robot to perform the robot-performable task; and
deploy the robot to perform the robot-performable task further based on receipt of user input indicative of actual interest of the user in deploying the robot to attend the event in lieu of the user.

14. The system of claim 13, wherein the prompting is performed further based on a determination that an implicitly calculated measure of potential interest of the user in deploying the robot to attend the event satisfies an interest threshold.

* * * * *